(12) United States Patent
Moenckmeyer

(10) Patent No.: US 6,533,581 B1
(45) Date of Patent: Mar. 18, 2003

(54) DENTURE SET

(75) Inventor: Ulrich Moenckmeyer, Nierstein (DE)

(73) Assignee: Zahn Spektrum GmbH, Nierstein (DE)

( * ) Notice: Subject to any disclaimer, the term of this patent is extended or adjusted under 35 U.S.C. 154(b) by 0 days.

(21) Appl. No.: 09/530,079

(22) PCT Filed: Aug. 19, 1999

(86) PCT No.: PCT/EP99/06079

§ 371 (c)(1),
(2), (4) Date: Jun. 16, 2000

(87) PCT Pub. No.: WO00/10483

PCT Pub. Date: Mar. 2, 2000

(30) Foreign Application Priority Data

Aug. 20, 1998 (DE) .......................................... 198 37 748

(51) Int. Cl.[7] .............................................. A61C 13/08
(52) U.S. Cl. ...................................................... 433/197
(58) Field of Search ................................ 433/167, 171, 433/197, 198

(56) References Cited

U.S. PATENT DOCUMENTS

| 2,416,983 | A | * | 3/1947 | Dickson ...................... 433/197 |
| 2,620,562 | A | * | 12/1952 | Folson ........................ 433/197 |
| 3,105,300 | A | | 10/1963 | Beresin |
| 4,626,215 | A | | 12/1986 | Clarke |
| 5,326,262 | A | * | 7/1994 | Jorgenson |
| 5,733,125 | A | * | 3/1998 | Foser .......................... 433/197 |
| 5,951,289 | A | * | 9/1999 | Kura et al. .................. 433/197 |

FOREIGN PATENT DOCUMENTS

| DE | 195 08 762 C | | 5/1996 |
| DE | 297 16 622 U | | 1/1998 |
| DE | 29716622 | * | 3/1998 |

* cited by examiner

Primary Examiner—Todd E. Manahan
(74) Attorney, Agent, or Firm—Michael J. Striker

(57) ABSTRACT

The invention relates to a set of prefabricated teeth. The object of the invention is to make available a set of artificial teeth in which better adaptation of the artificial denture to the anatomical conditions of the patient, which are determined by the position of the condyles in the mandibular joint and their path of motion, is made possible. This object is attained by providing that the contact points between antagonist pairs of teeth are disposed on a sagittal and transversal compensation curve that is defined by the motion of the condyles of the mandible.

19 Claims, 10 Drawing Sheets

DENTURE SET

Figure 1:
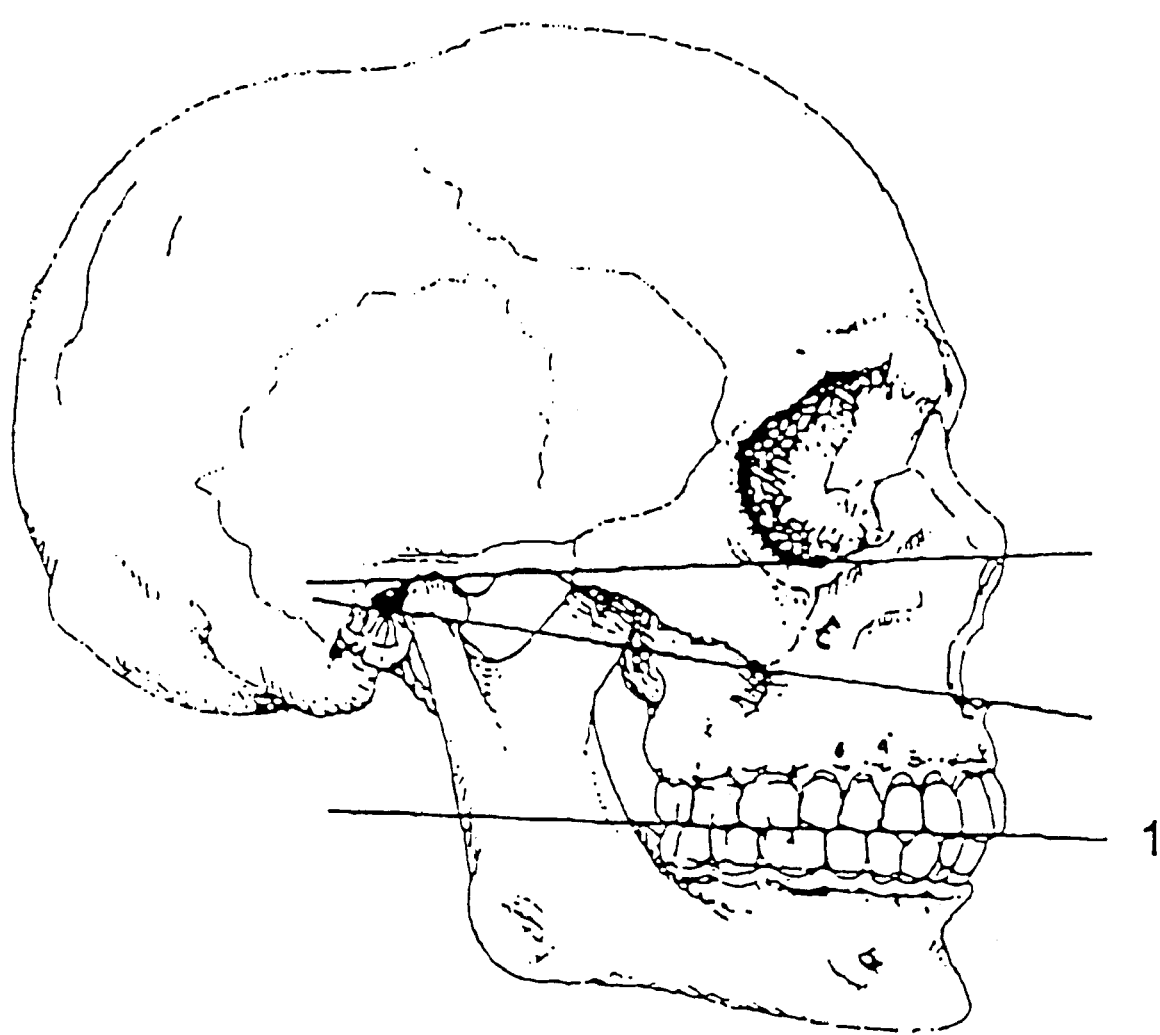

The invention relates to a denture set of prefabricated teeth, which has at least one first tooth, selected from a group of teeth intended for one jaw, and at least a second tooth selected from a group of antagonists intended for the other jaw, and the teeth have at least one contact point, on the surfaces disposed facing the antagonists, with which contact point the antagonist comes into contact.

Until now, in the production of dentures, the procedure was that first, from a prefabricated set of artificial teeth, the dental technician set up the individual teeth in an articulator on a wax model taken from the jaw of the patient. In this setting up process, he orients himself in accordance with certain principles. For instance, the edge of the side teeth, that is, the apexes of the tooth cusps, should be located on a line that corresponds to Spee's curve. The buccolingual cusp tangents should be inclined slightly, and increasingly from the second premolar to the second molar, toward the floor of the mouth. This is in accordance with Wilson's theory, according to which the tooth cusps should be located on a transversally extending curve. In the setup of the teeth, a cutout of a spherical dome can therefore be used, against which the teeth each come to rest with their upper edge. This procedure is in accordance with Monson's theory. After the setup of the teeth in wax, a trial of the wax model in the patient, and subsequent polymerization, the prosthesis is ground in an articulator, in order to adapt the engagement of the teeth of the upper and lower jaws. The goal here is to allow only point-type contacts rather than any contact surfaces. Another need is that the denture balance on both sides; that is, in the closed position with complete intercuspidation, the molars of the upper and lower jaws should mesh with one another on both sides and form contact points. This bilateral balancing, which is not in accordance with natural conditions, is intended to prevent the denture from being pried out and thus tilting out of the way in the intercuspidation position. This adaptation is done by having the dental technician, after he has set up the teeth, machine the chewing surfaces of the teeth by grinding them down until such time as the teeth of both halves of the jaw are balanced and the desired number of contact points has been achieved. Once this is finished, the denture is placed in the mouth of the patient and further machined by the dentist, until the patient has the subjective feeling of an acceptable adaptation of the denture.

In known false teeth, or dentures, the precise location of the contact points between the teeth of the upper and lower jaws is accordingly accomplished only during machining. Because of the machining during the adaptation, the vertical height is also reduced. The term "vertical height" is understood to mean the relative position of the upper and lower jaws, or in the final analysis the distance between the jaws, measured vertically. This distance is reduced, however, by the grinding down of the teeth during the adaptation of the denture. Thus during the construction and adaptation, the shape of the denture becomes farther and farther away from the natural conditions that are predetermined by the jaw itself. As a result, the location of the jaws relative to one another and thus the location of the condyles in the joint are determined by the positioning of the artificial teeth in the denture. This is contrast to natural conditions, in which the location of the condyles in the joint and the shape of the jaw in the final analysis determine the location of the teeth, because the teeth change their position until such time as they have adapted to the conditions predetermined by the jaws and the mandibular joint.

As a consequence, a number of problems arise in the dentures made with known artificial teeth, and these problems are a severe burden to the patient.

Since the position of the condyles in the joint is determined by the arrangement of the artificial teeth, the result, unless this position matches the natural one, is muscle stresses and pains, since the jaw is forced into an unnatural position in the closing position. To overcome this, the dentist grinds off further contact points. This further reduces the vertical height and hence under some circumstances shifts the condyles even farther out of their natural position. As a result, the patient can never have well-seated dentures; finally, the only remaining option is to remake the denture, yet once again the same difficulties stand in the way of a good denture fit.

Rapid denture wear is also caused by the shifting of the condyles out of their natural position that occurs in the intercuspidation position. During the process of closing of the jaw, while the tooth cusps are outside the closing position they meet the antagonist and then slide along its surface to reach the closing position. After being worn for only a short time, worn surfaces develop in the denture, leading to the formation of still more contact points or contact surfaces.

Since the final disposition of the contact points does not result until during the machining, it is moreover not assured that the forces initiated into the tooth will add up to a resultant in the direction of the tooth center line. Heavy loads in the tooth that have a horizontal force component can thus occur, which once again leads to premature wear of the denture.

A further disadvantage of this random arrangement of contact points is that in the closing motion, not all the contact points develop simultaneously. An excess number of contact points can also occur. As a result, the patient loses his feel for the closing position in the biting process, which is perceived as extremely irritating. Finally, contact points can also come to rest on oblique surfaces. There is then the risk in the closing motion that the antagonist will slip off, resulting in high peak loads on the tooth.

Previously known artificial teeth for a dental prosthesis or denture take the biomechanical conditions, which are predetermined by the motions of the jaw, into account only inadequately, if at all. For instance, the design of the denture set disclosed in German Patent DE 195 087 62 C2 is directed solely to the contacts between opposing teeth in a static state of maximal intercuspidation. The relationships of the tooth surfaces during the natural motions of the jaw remain unaddressed.

The object of the invention is therefore to furnish a denture made of artificial teeth in which better adaptation of the denture to the anatomical conditions of the patient, which are determined by the position of the condyles in the mandibular joint and by their path of motion.

In a denture set of the generic type in question, this object is attained by the bodies of claims 1 and/or 9 and/or 10 and/or 13.

In particular because at least three contact points (5) are provided in each fossa of a respective molar or premolar, with which contact points a chewing cusp of the antagonist comes into contact in the intercuspidation position, a substantially better prosthesis is obtained. The molars develop a plurality of contact points, while only one or two contact points are developed between the canines and incisors.

If at least five contact points per molar or premolar are provided, then each premolar or molar, with its chewing cusp, forms a common contact point with the chewing cusp of the antagonist.

Since until now the upper edge of the artificial teeth was disposed on the compensation curves, the location of the contact points was indeterminate. In the denture set of the invention, the location of the contact points is predetermined in that the contact points are disposed on a sagittal compensation curve and transversal compensation curve that are determined by the motion of the condyles of the mandible. The positioning of the artificial teeth is therefore determined by the location and the curvature of the compensation curves and thus by the anatomical conditions of the jaw and the mandibular joint. Shifting of the tooth along the mandibular arch in the distal or mesial direction is possible, with the contact points always located on the compensation curves. Upon shifting, there is accordingly no need to tolerate any loss of vertical height, either. The compensation curves can correspond to the curves of von Spee (sagittal) and Wilson (transversal), or the spherical curve of Monson, which forms a cutout from a spherical surface. As a result of the curvature of the compensation curve, the slope of the articulation path can be compensated for, and it is thus possible to adapt the denture to the angle of inclination of the cusps. The arrangement of contact points within one tooth should be as close as possible to a plane that is defined by the compensation curves of von Spee and Wilson or Monson. However, it should be taken into account that these curves are merely model concepts. It has been demonstrated, however, that slight deviations from the desired ideal state, which are due to individual anatomical differences among various patients on the one hand and to the need for a standardized tooth on the other, are compensated for by the relationships of the paired antagonists. Deviations on the order of magnitude of 5% of the tooth diameter are typical.

Since all the contact points are located at the same height, it proves to be a further advantage that in an opening motion, all the contacts between the molars of the upper and lower jaws are undone simultaneously, or in a closing motion are formed simultaneously. Especially in the latter type of motion, the result is a uniform force distribution on all the teeth; that is, peak forces, which are unavoidable if contact forms prematurely between individual teeth, do not occur.

Centering of the chewing cusp of the antagonist in the fossa of the artificial tooth is done by providing three contact points in the fossa of the tooth, at which contact points, in the intercuspidation position, a chewing cusp of the antagonist comes to rest. The contact points form a triangle, whose surface is disposed virtually perpendicular to the tooth center line. A slight inclination of the triangular surface is due to the location of the contact points on the compensation curves, which approximately form a cutout from a sphere.

The apex of the chewing cusp can slide harmonically into the intended stop position, if the contact points provided in the fossa are disposed on a spherical surface. Because of the spherical surface, there is no need for the apex of the chewing cusp to move along an exactly predetermined path into the closing position. Minor deviations from the intended path are tolerable, and the apex of the chewing cusp is directed into the closing position by sliding with its lateral surfaces along the spherical surfaces.

The apex of the chewing cusp is prevented from slipping off if in the fossa, tripodal ridges and/or marginal ridges are provided, and the contact points are disposed on the inclines of the tripodal ridges and/or marginal ridges.

A harmonic opening motion is made possible if adjacent to the tripodal ridges and originating at the contact points, concavities are provided in the direction of the laterotrusion and/or protrusion and/or lateroprotrusion and/or mediotrusion and/or surtrusive retrusion motion of the lower jaw. The apex of the chewing cusp can then move away from the stop position, in all the natural directions of motion of the jaw, without colliding with obstacles formed by shearing cusps or a marginal ridge.

Good chewing action is brought about if that the ratio of the surface area, formed by the circumference of the tooth in plan view, to the inside surface area of the occlusal table is 55–65%.

The positioning of the artificial tooth in the vertical direction is made easier in that a marginal ridge contact is provided on the mesial and/or distal marginal ridge of the tooth. The marginal ridge contact is located at the highest point of the marginal ridges. When the teeth are set up, the marginal ridge contacts of adjacent teeth can be aligned at the same height, and a result, because of their three-dimensional relationship to the marking, all the contact points necessarily come to rest on the compensation curves. Aligning the teeth by means of the apexes of the cusps is thus omitted.

Setting up the artificial teeth in the denture set is further facilitated in that the distal surface of the tooth is embodied as a shaped surface, preferably as a convex surface, and the mesial surface of the adjacent tooth is embodied as a fitting surface, preferably a concave surface. Because of the design of the contacting surfaces of adjacent teeth, the teeth necessarily enter the correct position relative to one another.

The correct setup of the artificial teeth is further facilitated in that the teeth, viewed from the buccal or labial direction, have a tooth center line that is disposed perpendicular to the occlusion line.

By a combination of marking, the design of the adjacent surfaces of adjacent teeth, and the orientation of the tooth center line, the necessary information for disposing the contact points in a certain plane can therefore be built into the artificial tooth. In setting up the teeth, the dental technician is thus provided with aid in the form of the shape of the teeth, so that correct positioning of the teeth can be achieved easily.

The denture set of the invention can be used both for a front- or canine-tooth-guided occlusion and for a both unilateral and a bilaterally balanced occlusion, if on the working side the molars of the upper jaw have guide faces on the buccal inclines that interact with the guide faces provided on the buccal outer surface of the molars of the lower jaw, and guide faces that interact with the guide faces provided on the palatal inclines of the molars of the upper jaw are disposed on the balance side of the buccal inclines of the molars of the lower jaw. For a balanced occlusion, the canine tooth is correspondingly ground down or tilted outward. Upon a lateral motion of the lower, all the molars then always have contact with their antagonists. This prevents the denture from being tilted away by unilateral loads.

In the case of canine-tooth guidance, an unhindered opening motion is made possible if the first premolar of the upper jaw has a buccal-mesial concavity, disposed between the tripodal bead and the marginal bead, that interacts with a guide face provided distal-palatally on the canine of the lower jaw.

Front-tooth guidance is made possible if the upper incisor lingually has a guide face extending in the incisal direction from the contact point. In the opening motion, the contact point on the cutting edge of the incisor of the lower jaw can then slide along the guide face.

An adaptation in the position of the lower incisors to the inclination of the condyle path is made possible in that the lower incisor has a surface, labially adjoining the cutting edge, that is inclined by an angle of 20°–45° to the approximal tooth center line. The surface can be oriented parallel to the condyle path, thus assuring harmonic guidance in the opening motion by the lingual guide faces.

A further adaptation of the denture is possible if the upper incisor has a surface, palatally adjoining the cutting edge, that is inclined at an angle of 20°–45° to the approximal tooth center line.

The invention will be described in terms of a preferred embodiment in conjunction with a drawing, and further advantageous details can be learned from the drawing figures. Functionally identical elements are provided with the same reference numerals throughout.

Figure 2A:
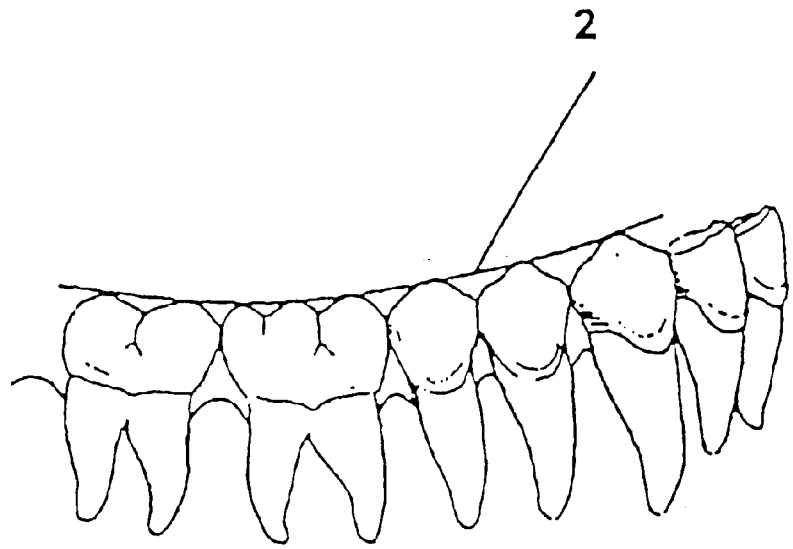
Figure 2B:
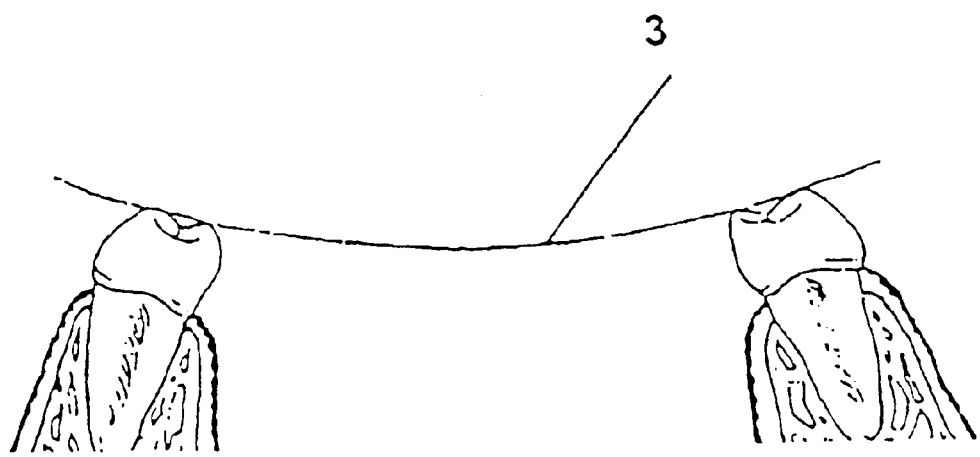
Figure 3:
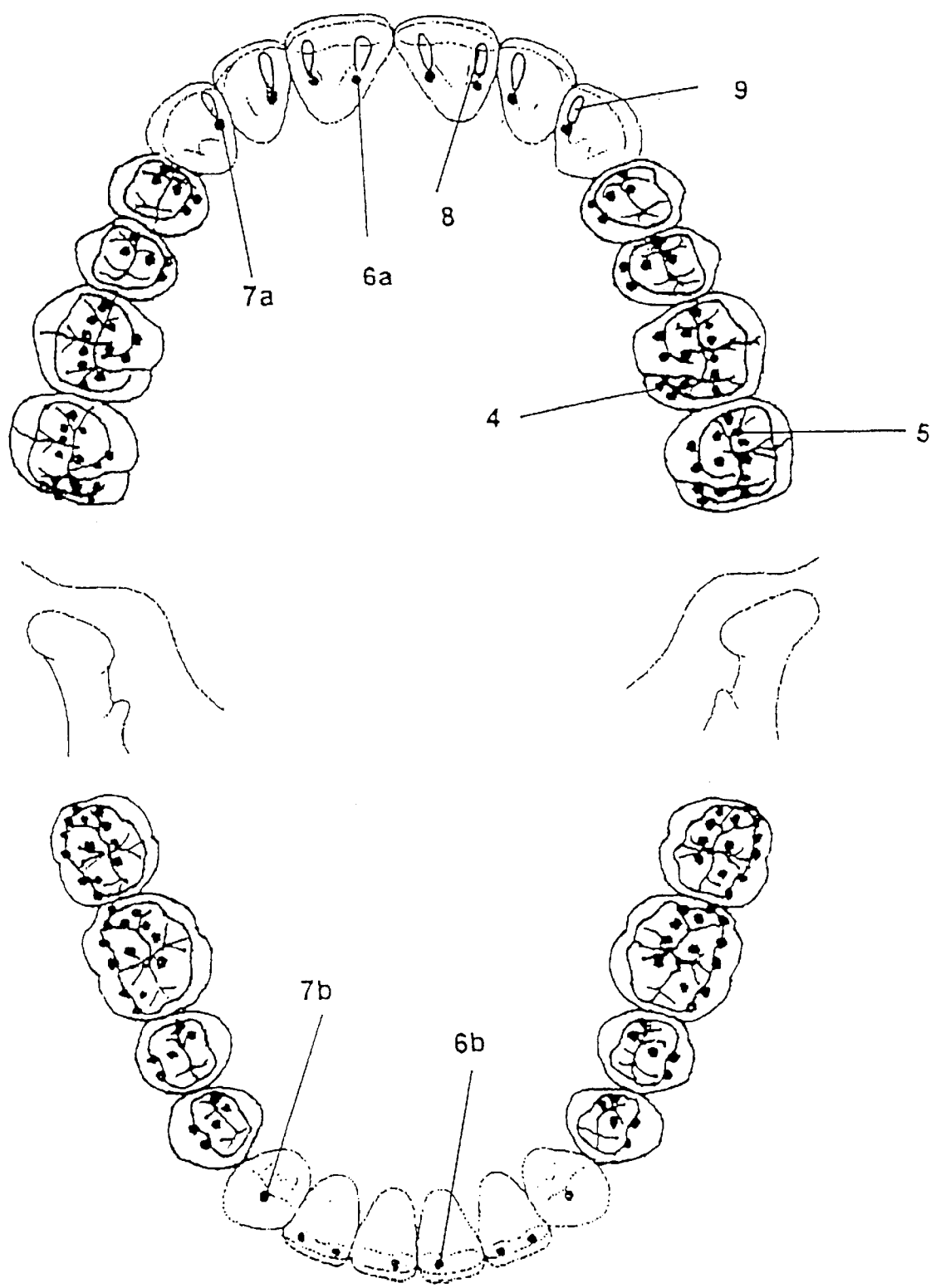
Figure 4:
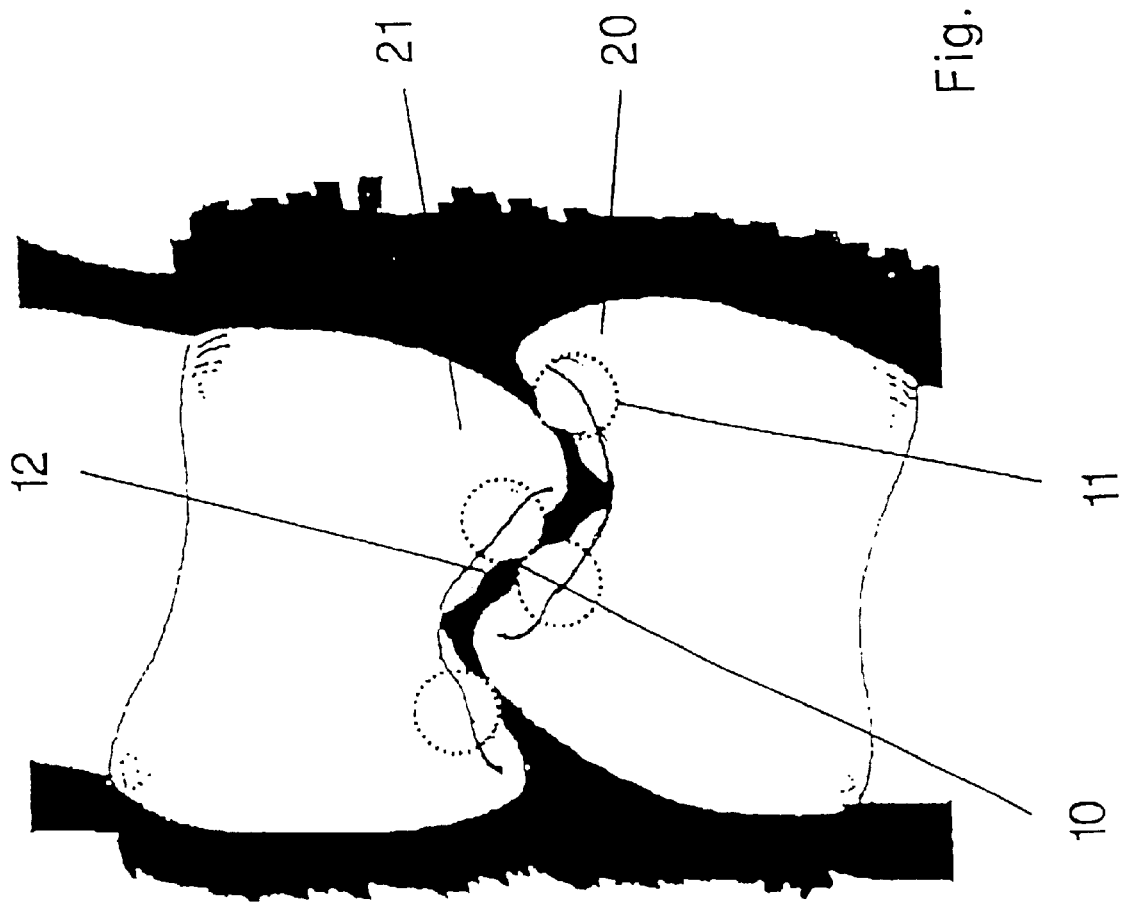
Figure 5A:
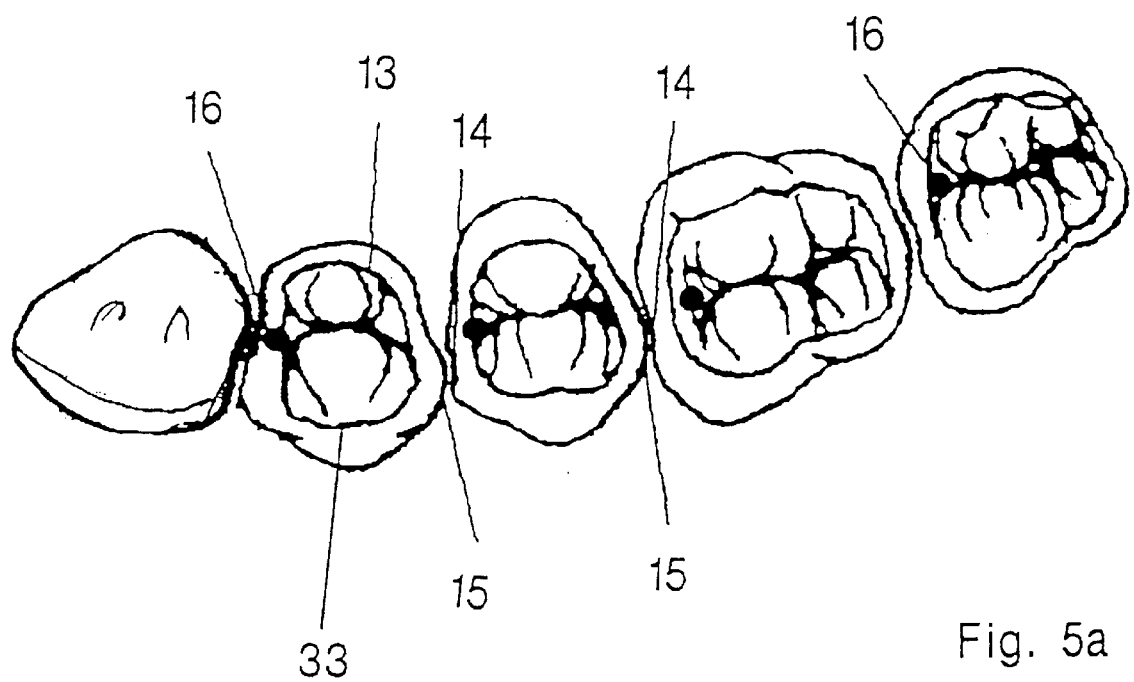
Figure 5B:
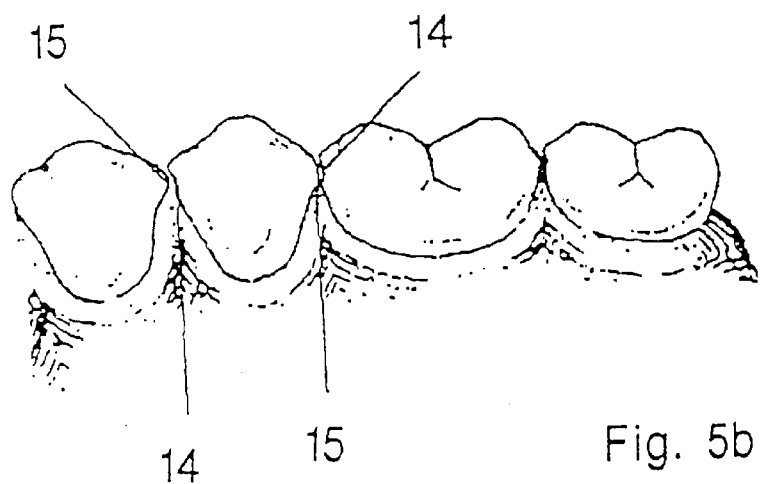
Figure 5C:
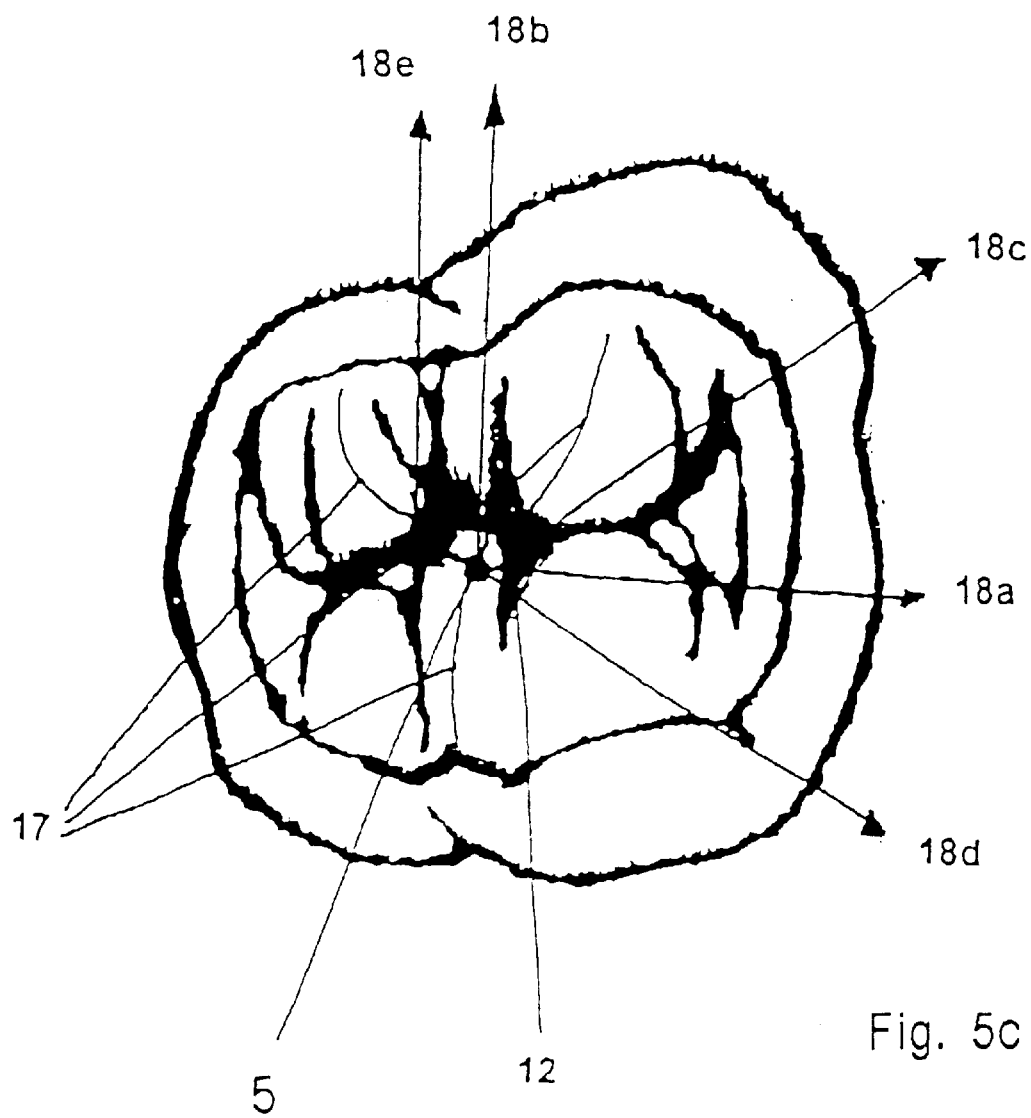
Figure 5D:
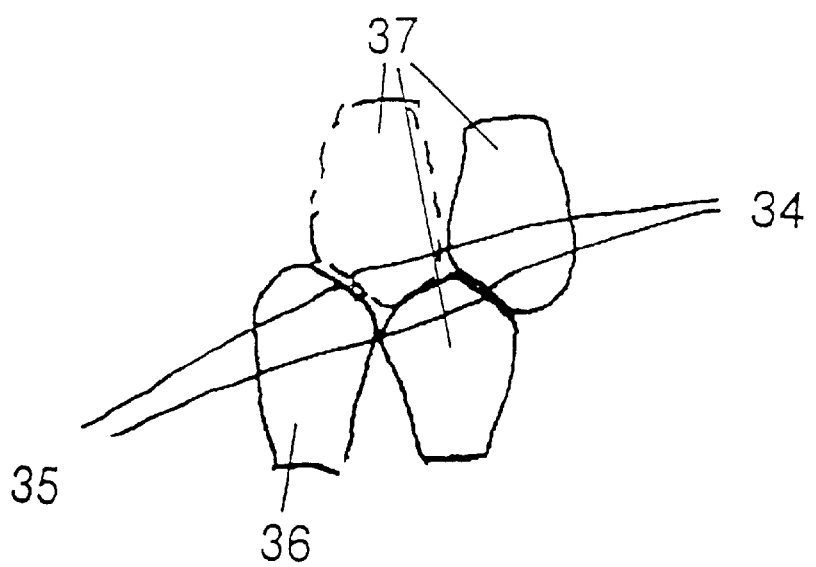
Figure 6:
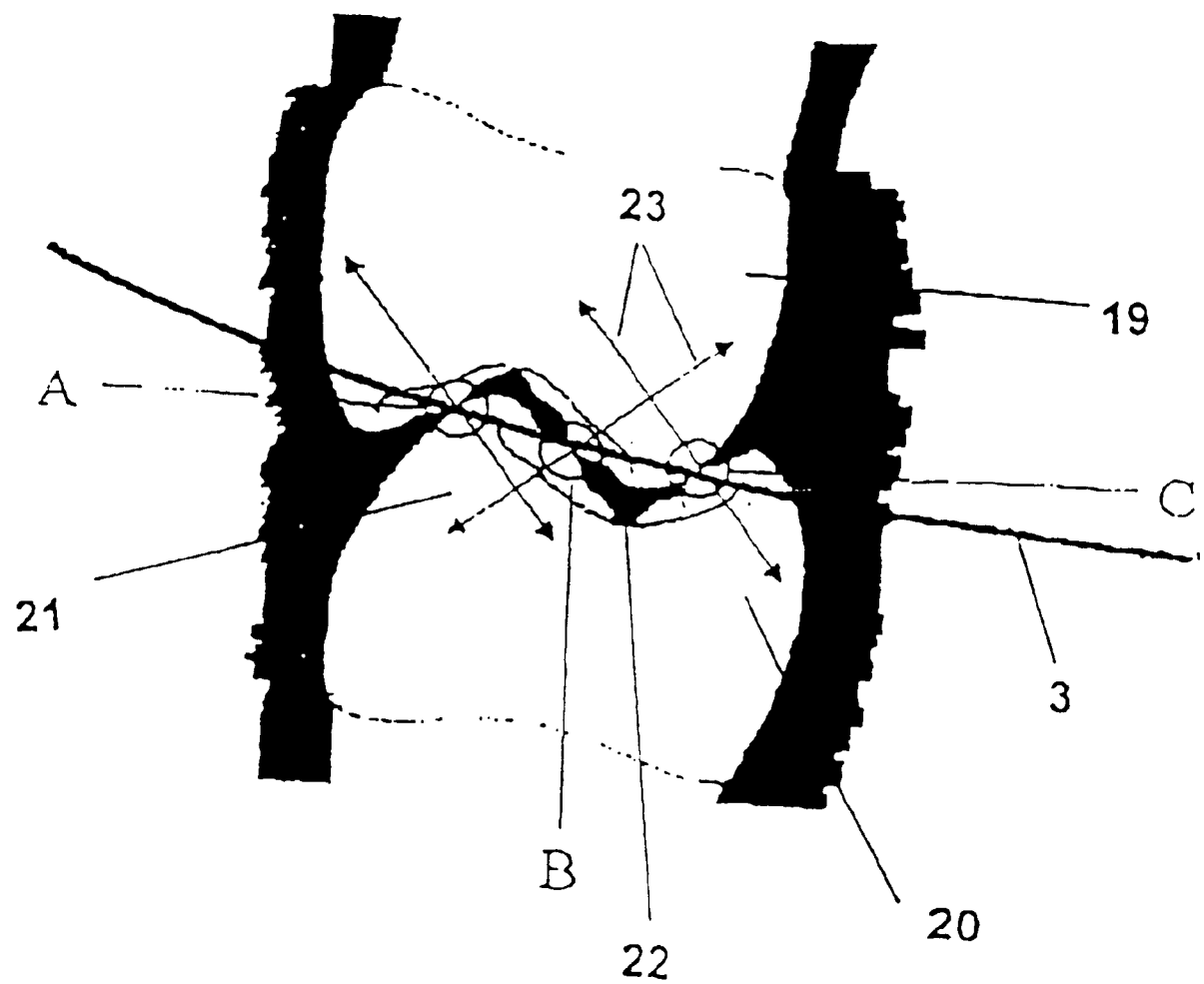
Figure 7:
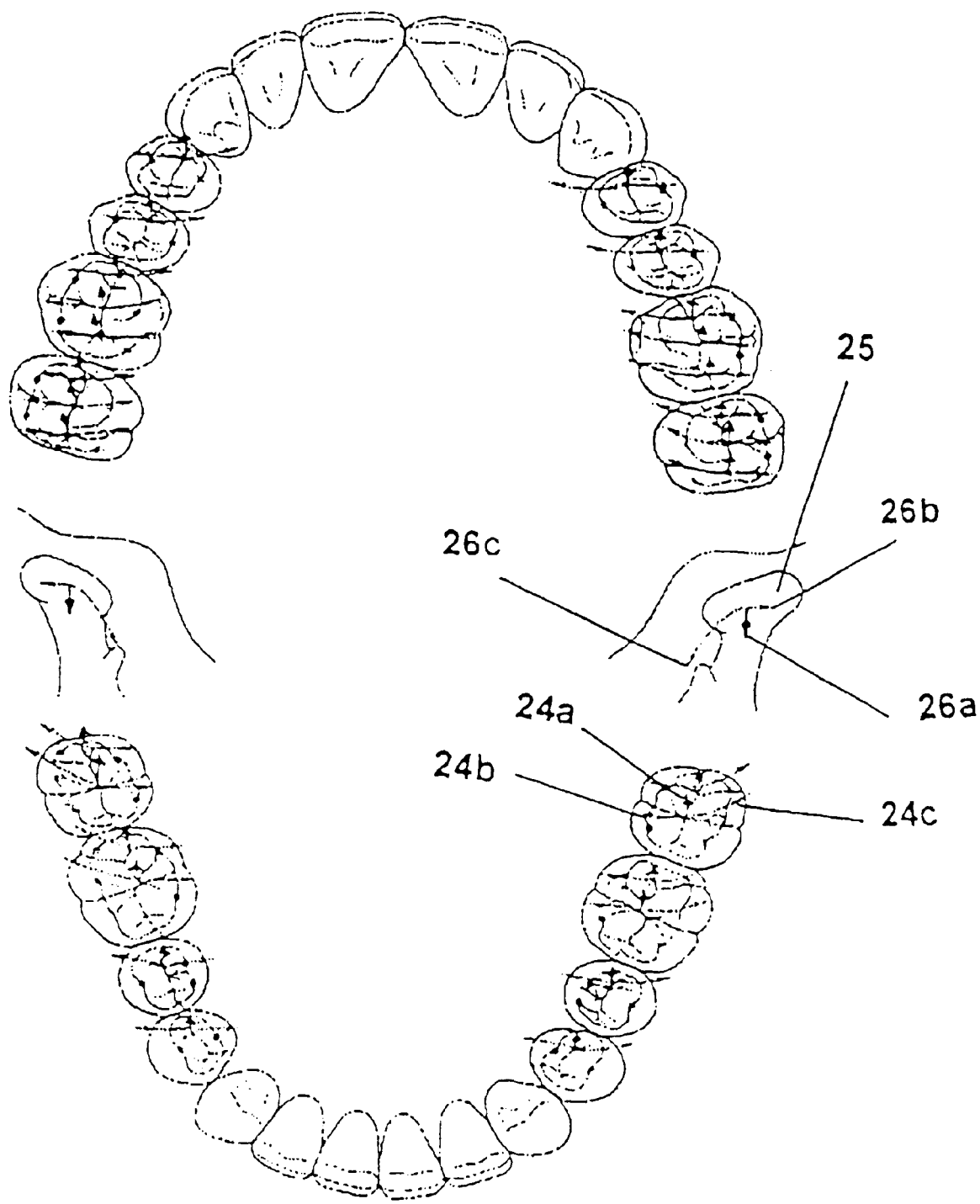
Figure 8:
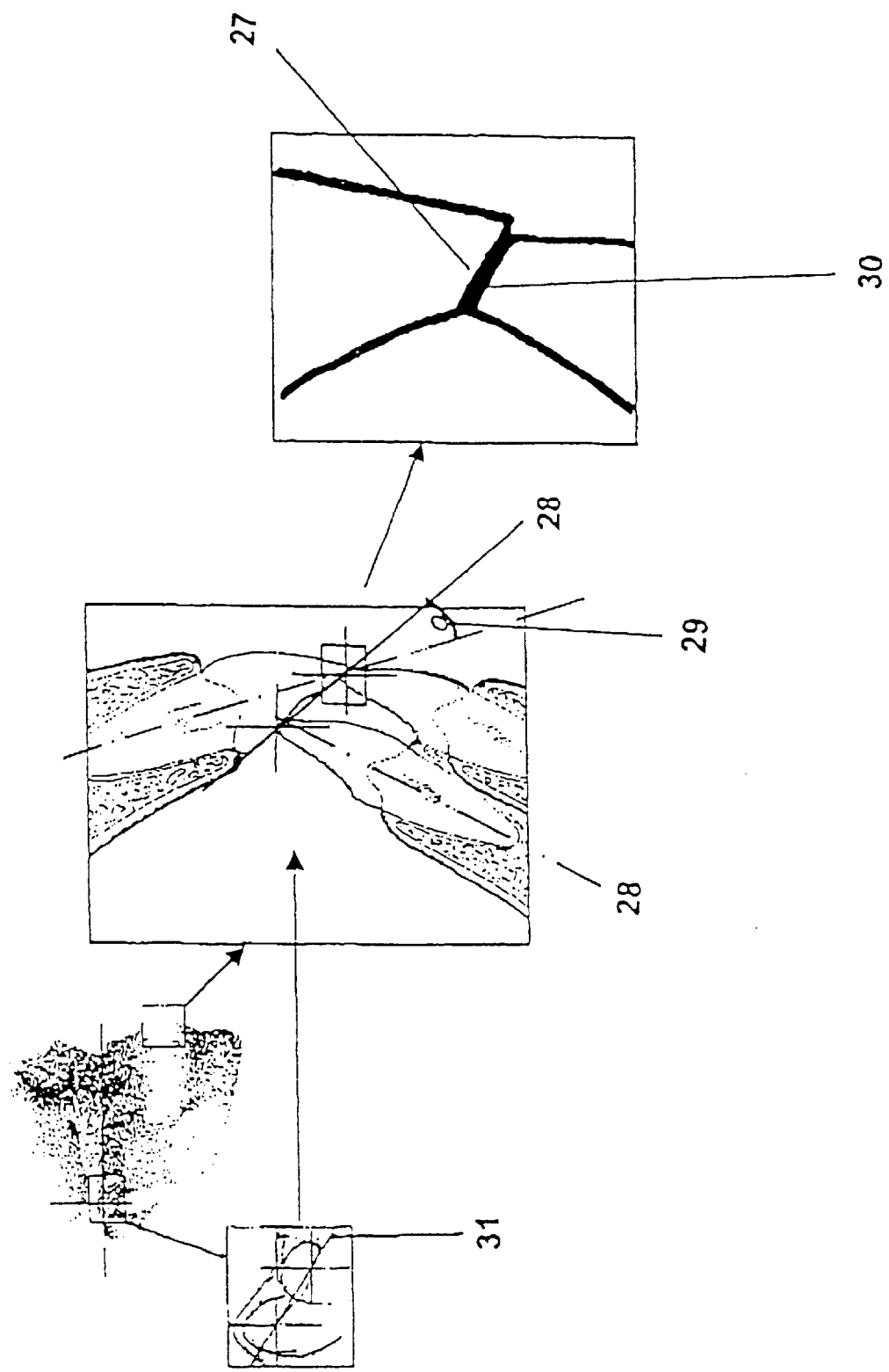
Figure 9:
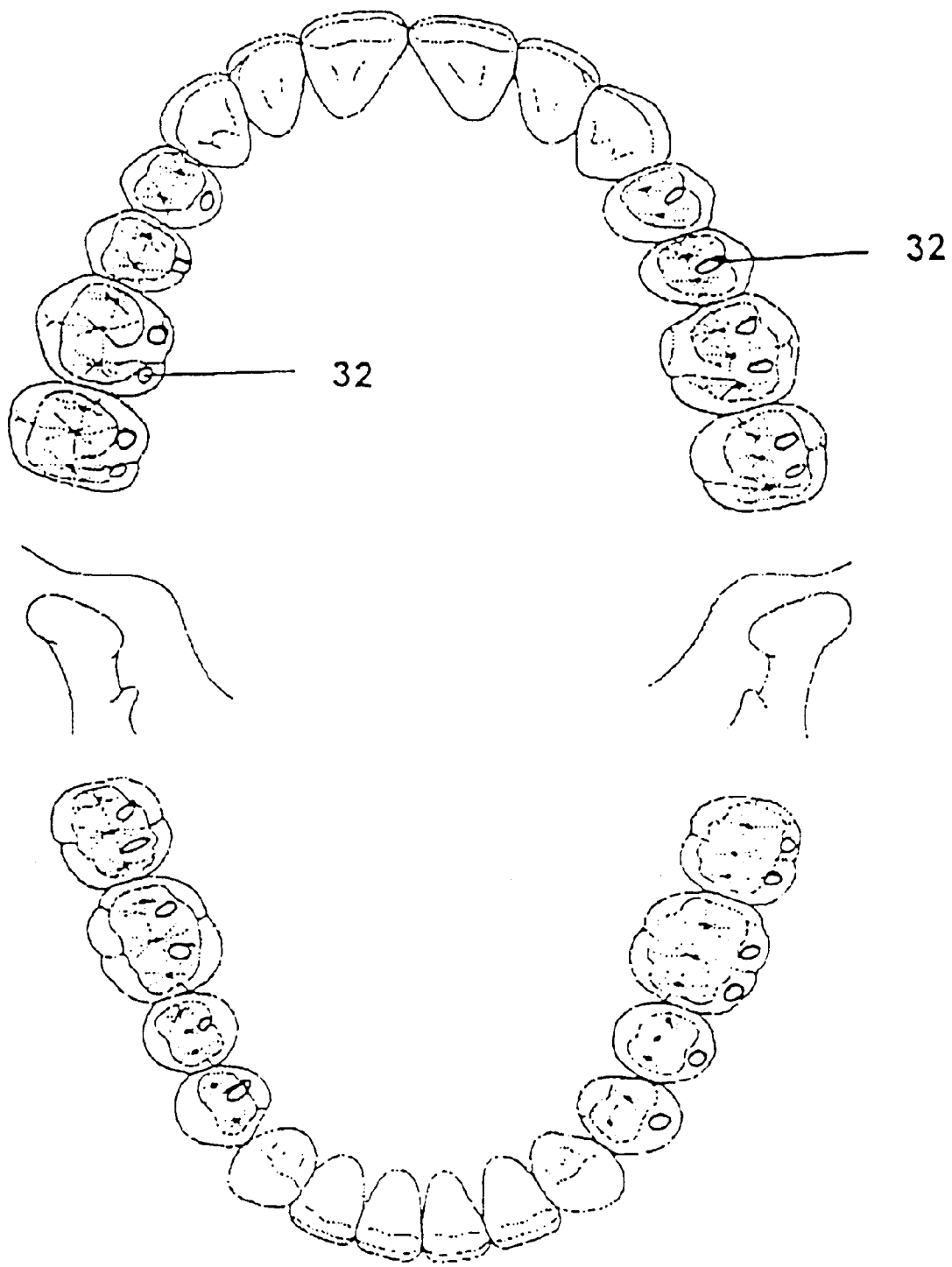

Individually, the drawings show:

FIG. 1: a side view of a human skull in which the occlusion plane is drawn in;

FIG. 2a: a schematic illustration of a detail from a human mandible, showing Spee's curve;

FIG. 2b: a schematic view of a section through a human mandible, showing Wilson's curve;

FIG. 3: a plan view on the upper and lower jaws, showing the disposition of the contact points on the chewing surfaces of the teeth;

FIG. 4: a schematic illustration of a view of a molar and its antagonist in a state of complete intercuspidation, seen from the approximal side;

FIG. 5a: an occlusal view of the premolars and molars;

FIG. 5b: a view of the premolars and molars from the buccal side;

FIG. 5c: an occlusal plan view on a molar;

FIG. 5d: an occlusal side view of the canine tooth and premolar;

FIG. 6: a schematic illustration of a view of a molar and its antagonist with complete intercuspidation, seen from the approximal side;

FIG. 7: a plan view of the upper and lower jaws, showing the orientation of the concavities as a function of the directions of motion of the mandible;

FIG. 8: a side of the upper incisors in various phases of the opening motion;

FIG. 9: a plan view of the upper and lower jaws, showing the location of the guide faces when the front- or canine-tooth guidance is undone (balanced occlusion).

FIG. 1 schematically shows a side view of a human skull. The occlusion plane is indicated at 1. This is an imaginary line that is used for orientation purposes in the setup of the artificial teeth. It can be determined by known methods in the (toothless) patient and transferred to an articulator, in which the setup of the teeth is done. In setting up the teeth of the denture set of the invention, the tooth center lines are aligned perpendicular to the occlusion plane. In this operation, only the inclination of the tooth center line viewed buccally (side teeth) or labially (front teeth) is taken into account. An approximal inclination of the tooth center line remains unaddressed.

FIG. 2 shows the course of the sagittal and transversal compensation curves. The mandibular joint is not a simple hinge joint that merely executes rotary motions. In the opening and closing motion of the jaw, translational components occur along with the rotary component. The condyles of the mandible are therefore capable of shifting in the joint. Upon a protrusion motion, the mandible moves forward and downward. It is guided in that the lower incisors slide with their cutting edges along the palatal guide faces of the top front incisors. The mobility of the condyles directly influences the disposition and shape of the natural teeth. In the case of front- or canine-tooth guidance, all the molars of one jaw thus simultaneously lose contact with the molars of the other jaw in the opening motion. The chewing surface must also be designed in such a way that in protrusion, lateroprotrusion and laterotrusion motions, no collisions between the tooth cusps of opposed molars will occur, since this would lead to major exertions of force on the teeth and in an extreme case would cause tooth parts to chip off. The motions of the condyle in the joint must accordingly be taken into account in the setup of the artificial teeth. This is done by disposing the upper edge of the teeth on an arch-shaped curve.

FIG. 2a shows Spee's curve 2 (sagittal compensation curve). This is a curve extending in the mesio-distal direction, which is formed by the line connecting the cutting edges of the front teeth of the lower jaw and the apexes of the cusps of the side teeth of the lower jaw.

FIG. 2b shows Wilson's curve 3 (transversal compensation curve). It extends in the transversal direction and touches the apexes of the cusps of the teeth in the region of the side teeth. It is concave in the lower tooth arch and convex in the upper. In the lower tooth arch, it comes about by a uniform lingual inclination of the right and left molars, and in the upper jaw it correspondingly comes about as a result of a buccal inclination.

In Monson's theory, the transversal and the sagittal compensation curves are combined. According to this theory, the chewing surfaces of the teeth are disposed as if on the surface of a sphere. The tooth center lines are oriented such that both the lower and the upper axes converge at a point.

The teeth of the denture set of the invention are designed such that the contact points of the opposed teeth are all located on the compensation curve of von Spee or on the spherical surface of Monson. In contrast to known artificial teeth, the contact points are therefore predetermined by the shape of the teeth and do not come about first from the setup and machining of the teeth. Since all the contact points are located in a spherical plane, the contact closure necessarily occurs simultaneously for all the teeth as well. This assures a uniform distribution of force and a defined conclusion of the closing motion.

FIG. 3 shows a plan view on the rows of teeth of the upper and lower jaws. The numerals 4–7 designate the contact points between the teeth of the upper and lower jaws. In the side teeth, the chewing cusp of each of the molars engages the fossa of the antagonist. For each chewing cusp, three contact points are formed in the shape of a triangle (tripodization). The chewing cusps form contacts 4 on the marginal ridge and in the fossa. The contacts 5 in the fossa are each provided on tripodal ridges, which are not shown for the sake of simplicity. The triangular surface defined by a group of contact points 4, 5 is perpendicular to the tooth center line in each case. Because of the perpendicular orientation of the tooth center line on the spherical surface of Monson or the compensation curves of von Spee and Wilson, the contact points are aligned with the compensation curves.

In the region of the front teeth, with maximal intercuspidation, only one contact point 6a, b and 7a, b, respectively, is formed between the antagonist pairs. However, because of the different widths of the lower and upper incisors, there can be two contact points on each tooth that are then formed for different antagonists. The contact point 6a, 7a on the palatal side of the front teeth forms the starting point for a respective guide face 8, 9, along which the motion of the lower jaw is guided in the opening and closing motion, given incisor guidance 8 or canine guidance 9.

FIG. 4 schematically shows a view of a molar and its antagonist given complete intercuspidation, seen from the approximal side. The contact points in the fossa are each disposed on spherical surfaces 10. For the sake of clarity, the spherical surfaces are extended in dashed lines to form a circle 11. On both sides, the spherical surfaces 11 are adjoined by concavities 12, in which the apex of the cusp of the antagonist moves in the opening and closing motion.

In a closing motion, the apex of the cusp of the chewing cusp enters into the surface of a triangle formed by the contact points in the fossa of the antagonist. The wall of the apex of the cusp begins to interact with the spherical surface of a contact point of the antagonist and slides on it, until the wall also enters into interaction with the other two contact points. Centering of the cusp apex in the closing position occurs; in this position, the wall of the apex of the cusp contacts all three spherical surfaces 10 of the associated contact points (tripodization). In this way, centering in the horizontal direction is assured. The cusp apex has the freedom of executing tilting motions of the vertical axis in the closing position. The effect of this is that automatic alignment in the vertical direction is assured as well.

FIG. 5a shows a schematic plan view on the occlusal surfaces in the region of the side teeth. Reference numeral 13 indicates the boundary of the occlusal table, which is the boundary of the chewing surface. The mesial side of each of the molars has a concave surface 14, while a convex surface 15 is provided on the distal surface. These surfaces 14 and 15, which border one another between teeth located side by side, can also be seen in the buccal view of the side teeth in FIG. 5b. By means of the placement and shaping of the surfaces 14 and 15, a correct relation of the molars in the horizontal plane can be predetermined by the shape of the artificial tooth. On the mesial and distal sides of each tooth, a marginal ridge contact 16 is provided, by which the positioning of the teeth in the vertical direction can be predetermined. The marginal ridge contact is provided in each case at the highest point of the marginal ridge.

FIG. 5c shows an enlarged view of the occlusal surface of a molar; for the sake of simplicity, an occlusal compass is drawn in for only a single contact point. The disposition of the concavities 12, which is represented by the dark areas inside the chewing surface in the drawing, is due in each case to the occlusal compass. The concavities associated with a single contact point 5 extend, beginning at the contact point 5 disposed on the ridge spine 17, in the direction of the laterotrusion motion 18a, lateroprotrusion motion 18b, protrusion motion 18c, mediotrusion motion 18d, and surtrusive retrusion motion 18e of the lower jaw. These conditions must be met for all the contact points located in the fossa.

In FIG. 5d, which shows an occlusal side view of the canine and the premolars, a different physiological bite position is represented by dashed lines. The upper first premolar of the upper jaw on the buccal-mesial side has a concavity 34, disposed between the tripodal ridge and the marginal ridge, that interacts with a guide face provided buccal-distally on the canine, or in another bite position on the first premolar, of the lower jaw. Until now, it was not possible to handle different types of bite. This characteristic has made it possible for the first time to do so.

FIG. 6 shows a view of an antagonist pair from the mesial direction given complete intercuspidation. Reference numeral 3 indicates Wilson's curve, on which all the contact points come to be located. The chewing cusp 19 of the upper jaw molar, in the intercuspidation position, engages the fossa 22 located between the shearing cusp 20 and the chewing cusp 21 of the antagonist. The apex of the tooth cup rests with its lateral inclines on the inclines of the fossa, or more precisely on the tripodal ridges and marginal ridges (not shown). At the positions marked A and C, a marginal ridge contact is formed on the buccal and lingual side by one antagonist, and a tripodal ridge contact is formed by the other antagonist. In the position marked B, both antagonists form a tripodal ridge contact. The force is consequently not transmitted via the apex of the tooth cusp, and the loads in the tooth are thus less. The same is true for the engagement of the chewing cusp 22 of the lower jaw molars. The forces introduced into the teeth, whose vectors are indicated by reference numeral 23, add up to a force in the direction of the tooth center line. The engagement of the chewing cusp with the fossa of the antagonist and the course of the force in the direction of the tooth center line assure buccolingual stability of the row of teeth and prevents tilting motions of the denture.

FIG. 7 shows a plan view on the rows of teeth in the upper and lower jaws; the course of motion of the chewing cusp apexes out of the closing position is shown. The course of motion is determined by the motions of the condyles in the mandibular joint. They are schematically combined in the occlusal compass. This compass is shown in FIG. 7 for each chewing cusp of the antagonist; for the sake of simplicity, only the protrusion direction 24a, laterotrusion direction 24b, and lateroprotrusion direction 24c are shown. The motions originate at the triangular surface formed by three contact points each. For the sake of simplicity, this triangular surface is not shown in the drawing. Its center, however, is located at the starting point of each group of three arrows indicating motion. In the condyle 25, the respective courses of motion are shown with their horizontal component. The direction of motion of the condyle 27 is designated as 26a in the event of a protrusion, 26b in the event of a laterotrusion, and 26c in the event of a lateroprotrusion. The course of motion of the chewing cusp apex out of the closing position in the fossa of a molar occurs accordingly. To represent this, the direction of the protrusion for a molar is indicated at 24a, the laterotrusion at 24b, and the lateroprotrusion at 24c. The concavities 12, indicated in FIG. 5c to represent a certain molar, each extend along the path of motions 24 of the chewing cusp.

FIG. 8 shows a side view of a pair of incisors. On the palatal side of the upper incisor, a surface 27 is provided that adjoins the cutting edge. With the approximal tooth center line 28, it forms an angle of about 30°. Labially, a surface 30 is provided on the lower incisor that adjoins the cutting edge and forms an angle of about 30° with the approximal tooth center line. With the aid of these surfaces, by varying the inclination of the approximal tooth center line to the vertical, the slope of the articulation path 31 can be compensated for, and a harmonic opening and closing motion with front-tooth guidance can thus be achieved.

The artificial teeth of the exemplary embodiment are suitable for constructing a denture with both front-tooth and canine guidance and with balanced occlusion. Until now, balanced occlusion has been predominantly preferred in constructing dentures, since in this version, prying out of the denture during chewing motions can largely averted. To achieve a balanced occlusion, either the upper canines must be machined by grinding in order to overcome the canine guidance, or the canines must be tilted slightly outward.

In the balanced setup, the side teeth remain in contact during the shifting. Accordingly, contact points are developed not only in the closing position.

FIG. 9 shows a plan view on the rows of teeth of the lower and upper jaws. Reference numeral 32 indicates the sliding faces along which the various antagonist pairs are shifted in a lateral motion.

The denture set of the invention allows a setup of the teeth for both front-tooth and canine guidance and for balanced occlusion. By the shape of the teeth, the correct setup of the teeth is predetermined, so that the denture can be adapted very easily to the data taken from the patient. Various positions of the antagonist pairs can be achieved by the predetermined location of the contact points. The contact relation is thus not limited to a particular of antagonists. The rows of teeth can also be shifted by one-half of the width of one tooth in the mesial or distal direction, without loss of the correct contact relationship. For instance if space is very tight, compensation can be achieved by omitting one side tooth yet still preserving the correct contact relation.

The setting up of the teeth is done in such a way that first the rows of teeth of the lower jaw are set up, progressing distally from the front incisors. The location of the contact points is predetermined by the shape of the teeth, and the perpendicular orientation of the tooth center lines in the side region to the occlusion plane is predetermined. The tooth position of the upper jaw is obtained by placing the molars of the upper jaw on the antagonists of the lower jaw. After being checked in the patient's mouth and polymerization, the teeth need practically no further grinding.

What is claimed is:

1. A denture set of prefabricated teeth, having at least one first tooth, selected from a group of teeth provided for a first jaw, and at least one second tooth, selected from a group of antagonists provided for a second jaw, wherein the at least one first tooth has at least one first contact point (4–7) on surfaces disposed facing the antagonists, wherein said at least one second tooth comes into contact with said at least one first contact point, wherein at least three contact points (5) are provided in a fossa of a respective molar or premolar, wherein a chewing cusp of the at least one second tooth comes into contact with said at least three contact points (5) in a intercuspidation position, wherein said at least one contact point (4–7) is disposed on a sagittal compensation curve (2) and a transversal curve (3), wherein said sagittal compensation curve (2) and said transversal curve (3) are determined by a motion of at least one condyle of a mandible (25).

2. The denture set of claim 1, wherein at least five contact points are provided on each said molar or premolar.

3. The denture set of claim 1, wherein the teeth, viewed from a buccal or labial direction, have a tooth center line that is disposed perpendicular to an occlusion line (1).

4. The denture set of claim 1, wherein the at least three contact points (5) provided in the fossa are disposed on a spherical surface (10).

5. The denture set of claim 1, wherein tripodal ridges (17) and/or marginal ridges (33) are provided in the fossa, and the at least three contact points (5) are disposed on inclines of the tripodal ridges and/or marginal ridges.

6. The denture set of claim 1, wherein, adjacent to tripodal ridges of said fossa and originating at the at least three contact points (5), concavities (12) are provided in a direction of a laterotrusion or protrusion or lateroprotrusion or mediotrusion or surtrusive retrusion motion of one of said first or second jaw.

7. The denture set of claim 1, wherein a ratio of the surface area formed by a circumference of the at least one first and second tooth to the inside surface area of an occlusal table (13) is 55–65%.

8. The denture set of claim 1, wherein a marginal ridge contact (16) is provided on a mesial and/or distal marginal ridge of the tooth.

9. The denture set of claim 1, wherein a distal surface of said at least one first and second tooth is a shaped, convex surface (15), and wherein a mesial surface of an adjacent tooth is a concave fitting surface (14).

10. The denture set of claim 1, wherein an upper first premolar of an upper jaw buccal-mesially has a concavity (34) disposed between a tripodal ridge and a marginal ridge, wherein said concavity interacts with a guide face (35) provided buccal-distally on a canine tooth or a first premolar of a lower jaw.

11. The denture set of claim 1, wherein on a working side, molars of an upper jaw have first guide faces (32) on buccal inclines that interact with second guide faces (32) provided on a buccal outer surface of the molars of a lower jaw, and wherein third guide faces that interact with fourth guide faces (32) provided on palatal inclindes of the molar of the upper jaw are disposed on a balance side of the buccal inclines of the molars of the lower jaw.

12. The denture set of claim 1, wherein a first premolar of an upper jaw has a buccal-mesial concavity disposed between a tripodal ridge and a marginal ridge, wherein said concavity interacts with a guide face provided distal-palatally on the canine tooth of a lower jaw.

13. A denture set of prefabricated teeth for incisors and/or canines, having at least one first tooth selected from a group of teeth provided for a first jaw, and at least one second tooth selected from a group of antagonists provided for a second jaw, wherein the at least one first tooth has at least one first contact points (6, 7) on surfaces disposed facing the antagonists, wherein said at least one second tooth comes into contact with said at least one first contact point, wherein said at least one contact point (6, 7) is disposed on a sagittal compensation curve (2) and a transversal curve (3), and wherein said sagittal compensation curve (2) and said transversal compensation curve (3) are determined by a motion at least one condyle of a mandible (25).

14. The denture set of claim 13, wherein the teeth have two contact points.

15. The denture set of claim 13, wherein an upper incisor lingually has a guide face (8) extending in an incisal direction from at least one second contact point (6a).

16. The denture set of claim 13, wherein a lower incisor has a surface (30) labially adjoining a cutting edge, wherein said surface is inclined by an angle of 20°–45° to an approximal tooth center line (28).

17. The denture set of claim 13, wherein an upper incisor has a surface (27) palatally adjoining the cutting edge, wherein said surface is inclined at an angle of 20°–45° to an approximal tooth center line (28).

18. The denture set of claim 13, wherein a distal surface of said at least one first and second tooth is shaped, convex surface (15), and wherein a mesial surface of an adjacent tooth is a concave fitting surface (14).

19. The denture set of claim 13, wherein the teeth, viewed from a buccal or labial direction, have a tooth center line that is disposed perpendicular to an occlusion line (1).

* * * * *